United States Patent
Koch et al.

[11] Patent Number: 6,123,902
[45] Date of Patent: Sep. 26, 2000

[54] DEVICE FOR HIGHLY SENSITIVE MAGNETIC DETECTION OF ANALYTES

[75] Inventors: Hans Koch; Hartmut Matz; Roman Kötitz; Dietmar Drung; Lutz Trahms; Werner Weitschies; Wolfhard Semmler, all of Berlin, Germany

[73] Assignee: Institut Fuer Diagnostik-Forschung an Der Freien Universitaet Berlin, Berlin, Germany

[21] Appl. No.: 09/147,093

[22] PCT Filed: Mar. 26, 1997

[86] PCT No.: PCT/DE97/00611

§ 371 Date: Oct. 7, 1998

§ 102(e) Date: Oct. 7, 1998

[87] PCT Pub. No.: WO97/40377

PCT Pub. Date: Oct. 30, 1997

[30] Foreign Application Priority Data

Apr. 18, 1996 [DE] Germany .............. 196 15 254

[51] Int. Cl.[7] .................. G01N 25/20; G01N 21/00; A01N 1/02; C12M 1/00; G01R 33/02
[52] U.S. Cl. .................. 422/50; 422/62; 422/63; 422/186; 422/186.01; 435/283; 435/287.1; 435/287.2; 324/244; 324/252; 324/256; 324/260; 324/262; 505/846; 209/223.1; 210/222
[58] Field of Search .................. 422/50, 62, 63, 422/186, 186.01; 435/283.1, 287.1, 287.2; 324/244, 252, 256, 260, 262; 505/846; 209/223.1; 210/222

[56] References Cited

U.S. PATENT DOCUMENTS

| | | |
|---|---|---|
| 4,913,883 | 4/1990 | Imai et al. . |
| 5,329,165 | 7/1994 | Kao et al. ............................ 307/91 |
| 5,406,201 | 4/1995 | Kiryu et al. ..................... 324/248 |
| 5,408,178 | 4/1995 | Wikswo, Jr. et al. ............ 324/201 |
| 5,437,276 | 8/1995 | Takada ........................... 128/653.1 |
| 5,486,457 | 1/1996 | Butler et al. . |
| 5,532,592 | 7/1996 | Colclough ........................ 324/248 |
| 5,891,031 | 9/1995 | Ohyu ............................... 600/409 |

OTHER PUBLICATIONS

Patent Abstracts of Japan, vol. 15, No. 507 (P–1291), Dec. 20, 1991 & JP 03 220442 A (TDK Corp) Sep. 27, 1991.

Valberg, Peter A.: "Magnetometry of Ingested Particles in Pulmonary Macrophages", Science 1984, vol. 424, pp. 513–516.

Philo, J.S.et al.: "High–sensitivity magnetic susceptometer . . ." Rev. Sci. Instrum., vol. 48, No. 12, Dec. 1977, pp. 1529–1536.

*Primary Examiner*—Christopher L. Chin
*Assistant Examiner*—Pensee T. Do

[57] ABSTRACT

An apparatus for the qualitative and/or quantitative measurement of analytes, in particular in biological samples by means of receptor ligand binding and having a magnetizing device for the production of a magnetic field at the location of the sample and with a detection device for measurement of magnetic properties of the sample is characterized in that the magnetizing device is spatially disposed with respect to the detection device in such a fashion that the magnetic field produced by the magnetization device at the location of the magnetization is attenuated by at least a factor of 10, and preferentially by a factor of 1000 or more, at the location occupied by the sample during the measurement, or in that a switching device is provided for which, throughout a predetermined time duration and in particular during the measurement phase of the detection device can switch-off the magnetic field of the magnetizing device at the location of the sample. In this fashion new types of measurements for magnetorelaxometric detection of analytes or for the detection of analytes by means of remanence measurements can be carried out in a routine and economical fashion in vitro or in vivo.

18 Claims, 4 Drawing Sheets

DEVICE FOR HIGHLY SENSITIVE MAGNETIC DETECTION OF ANALYTES

BACKGROUND OF THE INVENTION

The invention concerns an apparatus for qualitative and/or quantitative detection of analytes, particularly in biological samples, by means of receptor ligand binding using a magnetizing device for the production of a magnetic field at a location of the sample and having a detection device for measurement of magnetic properties of the sample.

Similar apparatus can be inferred from prior art through the description of a measurement procedure for execution on an appropriate apparatus in accordance with JP 63090765-A2.

Apparatus for the measurement of receptor ligand binding are based on the measurement of signals generated by signal producing labels with which structure-specific substances are marked. The most sensitive current apparatus are based on the detection of radioactive marking substances (Radio Immuno Assay, RIA). The utilization of radioactive labels has obvious disadvantages, for example problems with storage and disposal of the radioactive substances. In addition, this type of apparatus requires a device for separating the bound from the unbound labels. Without this separation, a quantitative prediction is generally not possible.

Alternative apparatus are based on the optical measurement of agglutination, fluorescence, and color reactions. (FIA, ELISA). Herein, one is dealing substantially with photodetectors. Separation is also normally required in these methods for quantitative analysis. On the other hand there are a large number of apparatus for the determination of magnetic properties of samples which, however, have generally not been applied to the direct detection of receptor ligand binding up to this point in time.

A number of apparatus are known in the art which are based on methods using magnetic labels. For example, application of a magnetic field causes motion of magnetically marked particles which can be observed using, for example, a laser. In addition, there are apparatus based on methods with which magnetic labels are utilized for separation of bound and unbound components. In contrast thereto, there are very few apparatus which are based on measurement of the magnetic properties of the sample.

JP 63090765-A2 describes a SQUID immuno assay method based on magnetically marked antibodies or antigens. Unbound portions must, however, be removed from the sample (separation) following the antibody-antigen reaction. An appropriate apparatus therefor must consequently contain a device for separating the bound from the unbound labels. The magnetization of the sample is measured subsequent to separation in the presence of a magnetic field, i.e. measurement of the magnetization takes place in the field.

U.S. Pat. No. 4,913,883 describes an apparatus for immuno-agglutination assay. Same is based on the measurement of the agglutination of antibodies marked with magnetic particles in the $\mu$m size range. The apparatus necessarily comprises a device for isolating the agglutinate and a device for transport of this agglutinate through the detection device using a fluid stream.

JP 3-220442 A discloses a measuring process for carrying out agglutination immuno-assays with which the amount of agglutination is antibody determined using a method for measurement of the particle size of agglomerated magnetic particles disclosed in the publication. The method consists of switching a magnetic field which penetrates the stationary fluid sample and measuring the residual magnetic flux density of the agglomerated magnetic particles.

In accordance with JP 3-220442 A determination of the degree of agglutination can also be carried out by means of optical processes for determination of particle sizes. Towards this end the published process solely concerns a method for the determination of the particle size of magnetic particles resulting from agglutination which can only be utilized in the manner described for agglomerates of magnetic particles, wherein the particle size of the agglomerate lies in the micrometer range.

A measuring process described in U.S. Pat. No. 5,486,457 serves for the determination of the mobility of magnetic particles bound to cells. The apparatus described therein measures magnetic fields in the presence of a weaker magnetic field which is rotated through 90° with respect to the magnetizing field.

An article by Valbeg et al. in Science 1984, volume 424, pp. 513–516 discloses a method based on magnetic field measurements under rotation of magnetic particles with particle sizes of typically 0.7 $\mu$m. Lock-in-technology is explicitly used to increase the measuring sensitivity. This is a modulation process with which the measured signal is recorded in a narrow band fashion.

The article by Philo et al. in Rev. Sci. Instrum. 1977, Volume 48, pp. 1529–1536 describes a process with which volume susceptibilities can be measured with the assistance of SQUID technology. Those advantages of SQUIDs for high-sensitivity measurements which could be useful to future instrumentation are explicitly mentioned.

The German patent applications DE 195 03 664.6 and DE 195 08 772.0, which do not constitute prior art, describe methods and compounds for the magnetorelaxometric detection of analytes or for the detection of analytes by means of remanence measurements. In the following, magnetorelaxometric detection designates the binding-specific detection of analytes in liquid or solid phase characterized by the use of ferro- or ferrimagnetic colloidal particles as a detectable magnetic marking for the detection of analytes by means of ligand receptor binding with relaxation of their magnetization being determined as the measured quantity. Below, detection of analytes by means of remanence measurement (also referred to below as measurements of the binding remanence) designates the binding-specific detection of analytes in liquid or solid phases characterized by the use of stable or quasi-stable ferro- or ferrimagnetic substances as detectable magnetic markings for the detection of analytes by means of ligand receptor binding with the remanence of their magnetization being determined as the measured quantity. In the latter two methods:

I) the relaxation (the time decay of the magnetization) of the sample is measured directly after switch-off or removal of the magnetic field or II) the frequency-dependent magnetization of the sample in the presence of a magnetizing field is measured or III) the binding-specific remanence of the sample is measured following magnetization.

Towards this end it is desirable to:

1. sufficiently suppress external interfering signals (for example power line hum, fluctuations in the earth's magnetic field) and to avoid production of internal interfering signals to the extent possible, 2. avoid difficult or expensive magnetic shielding, as well as 3. effect simple and rapid sample change.

A new type of apparatus is therefore needed to carry out the above mentioned new methods which facilitates highly sensitive quantitative and qualitative detection of receptor ligand binding through measurement of the magnetic properties of samples.

Since no apparatus of this type are currently known in the art which are suitable for a routine economical execution of the above described new procedures, it is the purpose of the present invention to introduce apparatus of the above mentioned kind with which these new types of measurements can be carried out.

In accordance with a first aspect of the present invention this purpose is achieved in that, with an apparatus having the above mentioned features, the magnetizing device is spatially disposed with respect to the detection device in such a fashion that the magnetic field produced by the magnetizing device at the location of the magnetization is attenuated by at least a factor of 10, preferentially by a factor of 1000 or more at the location occupied by the sample during the measurement.

SUMMARY OF THE INVENTION

In a second aspect of the present invention, the above mentioned purpose is achieved in that a circuit is provided for which can switch-off the magnetic field of the magnetizing device at the location of the sample for a predetermined amount of time, in particular during the measurement phase of the detection device, and a device is provided for moving the sample during the measurement phase of the detection device. In this fashion a remanence measurement is possible without a time changing magnetizing field. By means of averaging or filtering, the signal-to-noise ratio can be substantially improved in this embodiment. In addition, a simplification and automatization of the sample transport as well as an automatic operation of the entire measurement system with a large number of samples is facilitated.

It is thereby important with the associated apparatus that, although the sample is magnetized, measurement of the magnetic properties of the sample are carried out in the absence or with sufficient attenuation of the magnetizing field (measurement phase).

This can be achieved in accordance with the invention either through a spatial separation of the magnetizing device from the detection device or by means of a separation of the magnetizing process from the measurement in time.

Use of the device in accordance with invention for carrying out the new types of methods described above, has the particular advantage that the measured signal of bound magnetic markers can be clearly distinguished from the signal of unbound magnetic markers so that a separation of the unbound from the bound markers is not necessary. In addition, the binding dynamics can be investigated without changing samples.

The device according to the present invention also facilitates the simultaneous determination of a plurality of analytes in a complex sample (multianalyte assay) when carrying out the above mentioned new methods.

In the device according to the first aspect of the invention, the spatial separation of the magnetizing device from the measuring location facilitates extremely high magnetizing field strengths without influencing the detection device. Magnetization can already begin during the binding process. Sample preparation can be done away from the measuring location, for example in different laboratories or even in different cities. Permanent magnets can also be utilized for magnetizing which do not require the input of energy during the magnetizing phase.

In the device in accordance with the above described second aspect of the invention, the field necessary for magnetizing the sample can be switched-off so that measurements can be carried out in the absence of the magnetizing field.

An embodiment of the apparatus in accordance with the invention is particularly preferred with which the detection device includes a device for measuring the magnetization of the sample. The magnetization is the measured quantity which can be most sensitively measured in these types of samples.

Another embodiment is also advantageous with which the detection device includes a device for measuring the binding remanence of the analyte in the sample. The measurement of the binding remanence facilitates a multianalyte assay. In addition, sample preparation can be carried out away from the measuring location, for example, in different laboratories or in different cities. This type of measurement also achieves a high detection sensitivity, with sample preparation and the measurement procedure being relatively simple. Measurement of the binding remanence can also be utilized for in vivo investigations.

An in vivo application is also possible in an embodiment of the device in accordance with the invention with which the detection device includes a device for magnetorelaxometric detection.

This device facilitates short measurement phases which, for example, allow for studies of reaction dynamics in a sample with high time resolution.

An embodiment is highly preferred with which the detection device includes at least one SQUID (superconducting quantum interference device) as part of the magnetic field sensor, since SQUIDs are the most sensitive type of magnetic field sensor currently known.

In an additional embodiment, the detection device includes at least one induction coil as part of the magnetic field sensor. This type of induction coil is simple to construct, economical to produce and relatively sensitive at high frequencies.

In a third aspect of the invention a circuit is provided for switching-off the magnetic field of the magnetizing device at the location of the sample, in particular, during the measurement phase of the detection device and the circuit includes a first device for switching-on and -off the magnetic field produced by the magnetizing device as well as a second device for switching-on and -off the detection device.

In a first improvement of this embodiment of the invention, the first and second devices can be switched independently of each other. In this fashion measurement can be started after switching-off the magnetic field and after a suitable time delay.

In an alternative improvement of the above embodiment, the first device can be switched in predetermined fixed time correlation with respect to the second device. In this embodiment, a suitable choice of the switching time facilitates a filtering-out of processes having short time constants and thereby a selective signal detection. The switching-on of the measuring device at as early a time as possible which is facilitated thereby, additionally allows for improvement in the signal-to-noise ratio in relaxation measurements.

An improvement of the latter mentioned three embodiments of the invention is preferred with which the first device can produce predetermined field amplitudes and field polarities of the magnetic field produced in the magnetizing device. In this fashion the sample can be magnetized in a particularly directed fashion and the signal-to-noise ratio can be improved by time averaging over a plurality of periods. This can, e.g. be achieved through chopper operation. These embodiments are particularly well suited for carrying out multianalyte assays.

An improvement in the latter embodiment provides that the first device can produce predetermined time varying amplitudes and predetermined time varying polarities of the magnetic field produced by the magnetizing device. This facilitates remanence measurements without spatial motion of the sample. The binding remanence measurement principle can therefore also be utilized for the case of in vivo measurements. In addition, multianalyte assays are possible. Constant or stationary interfering fields can also be easily compensated. The signal-to-noise ratio can be improved to a further extent through comparative measurements and averaging procedures. Measurement of the magnetization curve is also possible with the device and, finally, the SQUID system can be permanently operated in the FLL-mode more closely described below, whereby the applied magnetic field itself can be measured.

An embodiment of the apparatus in accordance with the invention is particularly preferred which provides for a device for the electronic suppression of interfering signals. In this fashion an even better signal-to-noise ratio is possible and non-shielded measurements can be carried out. Complicated and expensive shielding is therefore obviated. These type of apparatus can furthermore be operated in practically any environment. In addition, the results are largely site-independent.

In an improvement of this embodiment, the device for electronic suppression of interfering signals includes a device for adaptive filtering. This facilitates an even better signal-to-noise ratio, since interfering signals are actively suppressed. Adjustment to the excitation signal also allows for increased detection sensitivity.

An embodiment of the apparatus in accordance with the invention is also particularly preferred which provides for a device for the measurement of interfering fields and a device connected thereto for corresponding compensation of the signal measured by the detection device and/or of the magnetic field produced by the magnetizing device. Recognition of the direction of the interfering field facilitates a substantially better balancing of the apparatus. In addition, the speed of signal change of the sensor SQUIDs can be improved and a checking of the homogeneity of the exciting magnetic field is facilitated.

The embodiments of the apparatus in accordance with the invention described above, in particular those suitable for measurement of the binding remanence or of the magnetorelaxometric detection can also, in particular, be adapted for in vivo measurements on people or on experimental animals.

Further advantages of the invention can be derived from the description and the drawing. The above mentioned features as well as those to be further described below can be individually or collectively utilized in accordance with the invention in arbitrary combination. The embodiments shown and described are not to be considered as exhaustive enumeration, rather have exemplary character only for illustration of the invention.

The invention is represented in the drawing and will be more closely described in connection with an embodiment.

DESCRIPTION OF THE PREFERRED EMBODIMENT

The following detectors are proposed for measurement of the magnetic field produced by binding of magnetically marked structure-specific substances:

1. SQUIDs (high Tc as well as low Tc)
2. Induction coils (possibly in combination with a magnetic core analogous to the magnetic head used for magnetic tapes)
3. Flux gate sensors
4. Magnetoresistive resistors, in particular GMR sensors Magnetic field detectors having very fine energy resolution are required in order to be able to detect the smallest amounts of bound analytes in a solution. This can, e.g. be accomplished with SQUIDs. These types of SQUIDS can, under certain boundary conditions, also be operated with relatively large magnetic fields and are suitable as detectors given the flexibility of the associated superconducting field detection coils. If appropriate these can also be replaced by other detectors (see above).

The preferred apparatus in accordance with the invention for solving the associated problem uses the same detector configuration for relaxation as for remanence measurements of the analytes. Measurement method specific differences are substantially related to the manner of magnetizing the sample and the operation mode of the detectors. For example, FIG. 1 shows a schematic diagram of one possible apparatus configuration in accordance with the invention.

Figure 1:
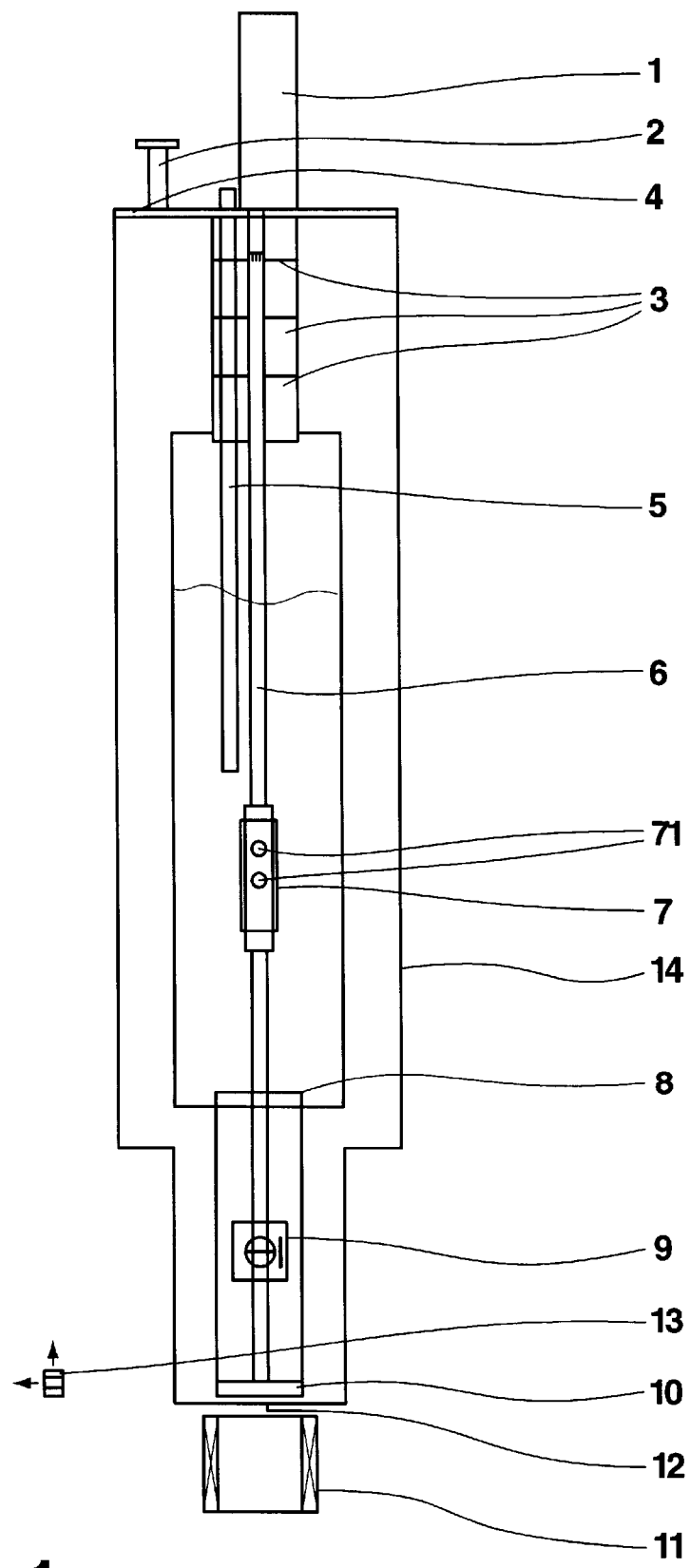
FIG. 1 shows a schematic longitudinal cut of a first embodiment of the apparatus in accordance with the invention.

In detail, FIG. 1 shows an electronic circuit 1 which is designated below as "FLL-electronics", since the SQUID can be operated in closed loop regulation mode (FLL-mode) therewith. Also shown is a vacuum connector 2, an arrangement of baffles 3, a Dewar lid 4, an overflow connector 5, a sensor mount 6, a magnetically shielded SQUID container 7, a field recording coil for the reference gradiometer 8, a vector magnetometer 9, a field recording coil for the sensor gradiometer 10, an excitation coil 11, a sample 12 as well as a position changeable compensation coil 13.

One or a plurality of SQUIDs 71 are utilized as sensors. Due to their principle of operation, it is necessary for the sensors to be operated in a cryostat 14 which holds the cooling liquid (liquid helium LHe or liquid nitrogen $LN_2$) to establish the superconducting condition. Alternatively, in embodiments not shown, the cooling can be effected by a refrigerator. Since the samples are usually present in liquid form, thermal insulation between the SQUID and the sample is necessary which, in the simplest case shown in FIG. 1, can be accomplished by means of the wall of the cryostat. In order to guarantee good magnetic coupling between the analytes in the sample and the field recording coil of the sensor gradiometer, the separation between same must be minimized, wherein the separation should preferentially be smaller than the effective diameter of the recording coil.

The liquid sample can also, if appropriate, be heated in order to prevent freezing of same; e.g. optically by means of a laser.

Normally conducting excitation coil 11 located outside of the cryostat 14 is usually utilized to magnetize the sample 12. A superconducting or a normally conducting coil can also be utilized inside the Dewar. In the above mentioned new measurement processes I and III (measurement of the relaxation and measurement of the time-independent remanence of the sample) the sample should be located in nearly magnetic field-free space during the measurement. This can be effected using compensation measures which will be more closely described below. A flux gate sensor or a movable field recording coil can be utilized as a reference sensor to determine the absolute magnitude of the field in the vicinity of the sample and appropriate site-dependent compensation coils 13 can compensate same (compensation of the interfering field).

In method II (measurement of the frequency-dependent magnetization of the sample), the sample is exposed to an alternating magnetic field which has changeable frequency. The excitation field should be homogeneous in the vicinity of the measuring volume.

The measured signal is coupled into the SQUID sensor by means of a suitable field recording coil (antenna). This antenna configuration is advantageously a planar gradiometer having two mutually compensating field coils of as similar a geometry as possible, wherein the coils can be connected in series or in parallel. The sample is advantageously disposed in such a fashion that same is enclosed by one of the coils or is located directly below same as shown in FIG. 1. A minimal separation between the active regions of the sample and the antenna coil is necessary for achieving very high measurement sensitivity. This can be achieved by minimizing the thickness of the cryostat wall in this region. The cryostat can have a substantially thicker wall away from the sample region.

The balance of the sensor gradiometer 10 (e.g. deviation of the effective directed surfaces of the two coils relative to the effective surface) caused by its geometry and the symmetry of the magnetizing field is of essential importance and can be improved by the coupling-in of a compensation field using the additional compensation coil 13 which can be controlled synchronously with the excitation coil 11. The compensation of the sensor gradiometer 10 in the magnetizing field can, e.g. be effected by means of a computer-controlled potentiometer or can be permanently aligned. Using a calibration without sample, the excitation coil is preferentially fed with an alternating current and the current through the compensation coil 13 is adjusted until a minimum signal results at the SQUID output. This configuration is maintained for the sample measurement. A phase correction must also be carried out if necessary.

These measures cause maximum suppression of imprecisions in the antenna coil geometry as well as asymmetries in the magnetizing field relative to the field recording coil and the measured signal becomes nearly independent of the time variation of the magnetizing field. In the event that unexpected balance displacements occur during the measurement or in the event that the compensation is not sufficiently precise, these errors can be compensated for e.g. by positioning the sample 12 under the other coil of the sensor gradiometer 10. In some cases it can be advantageous to not fully balance the sensor gradiometer 10 in order to maintain a measure for the strength of the magnetization.

These features facilitate:

1. measurement of the weak frequency-dependent magnetization of the sample in the presence of a strong alternating field and 2. measurement of the relaxation of the sample directly after switch-off of the magnetizing field, since the switching-off of the field itself no longer contributes to the measured signal.

One must take into consideration that the SQUID sensors 71 (or the Josephson contacts) themselves are magnetic field dependent and can displace their point of operation in an uncontrollable fashion in the event of excessively large magnetizing fields. In order to nevertheless guarantee a rapid tracking of the FLL-electronics 1 or a continuous measurement operation, the SQUID can be spatially displaced from the field recording coil as suggested in FIG. 1. Towards this end the SQUID can be positioned in the container 7 at some distance within a superconducting shield orthogonal to the magnetizing direction. The connection between the field recording coil and the SQUID can be effected e.g. by means of twisted superconducting leads which can also be magnetically shielded (lead capillaries). In addition a "demagnetization coil" can be utilized disposed about the superconducting shield (SQUID container 7) of the SQUID through which a portion of the exciting field current flows. The purpose of same is to reduce the field strength in the vicinity of the shield and to reduce the stray field produced by the magnetization. The superconducting shield and the demagnetizing coil should be disposed in such a fashion that the field distortions at the location of the field recording coil and the sample are minimized.

In order to achieve the highest possible field resolution of the measurement system and to attain a linear dependence between the output quantities and the measured magnetic field, the SQUID should, as already mentioned above, be operated in a closed regulating loop (FLL electronics 1). Towards this end the SQUID is utilized as a zero field detector. Each deviation from the zero field detected by the SQUID is oppositely coupled by means of the corresponding FLL-electronics 1 through production of a compensation field in the field recording coil. This signal is preferentially fed into the shielding via an appropriate coupling coil which is in series with the field recording coil. This method minimizes magnetic field distortions within the regulation range of the electronics.

The introduction of magnetically decoupled chambers into the shielding can prevent crosstalk of the opposite coupling signal onto the SQUID. In order to achieve an increased control region for the field recording coil 10 in the FLL-mode, it can be advantageous to only regulate out up to one or more flux quanta in the SQUID and then to induce gathering of flux quanta into the SQUID by resetting the integrator. The resulting flux quanta jumps must be counted in order to analyze the measurement with the magnitude of the output of the regulator then indicating the fraction of a flux quanta in the SQUID. In this fashion, the dynamic range of the SQUID regulation electronics can be substantially increased. In addition, in this manner the dynamic range of an A/D converter possibly required for analysis can be kept relatively small, since the high bit values are recorded with the counter.

In order to create an apparatus without expensive and difficult magnetic shielding, ambient interfering fields (e.g. power line hum and the earth's magnetic field) must be compensated for at the location of field recording coil 10. Towards this end a reference gradiometer 8 can be utilized at some distance from the first, disposed however with corresponding symmetry with respect to the excitation field. Subtraction of the output voltages of both gradiometers 8, 10 after the FLL-electronics 1 leads to an electronic gradiometer of higher order. These preprocessed signals can then be introduced to an A/D converter after appropriate computer-controlled offset compensation. In this fashion the required dynamic range of the A/D converter can be reduced. The output signal of the reference gradiometer 8 can be digitalized via a second equivalent data recording channel in order to achieve additional suppression of interfering signals through use of special filter algorithms (compensation of delay time differences, optimization filter, frequency band pass corrections and the like).

An electrical shielding of the SQUIDs and of the leads is advantageous (RF shielding). In most cases the superinsulation of the cryostat provides for sufficient shielding. The direction of interfering magnetic fields can also be measured with the assistance of the vector magnetometer 9 and an effective suppression of interfering fields achieved. In addition, all interferences caused by the magnetizing of magnetic objects located in the surroundings are to be avoided through appropriate choice of materials used in construction of the apparatus or are to be determined through appropriate calibration measurements and taken into account in the analysis.

Figure 2:
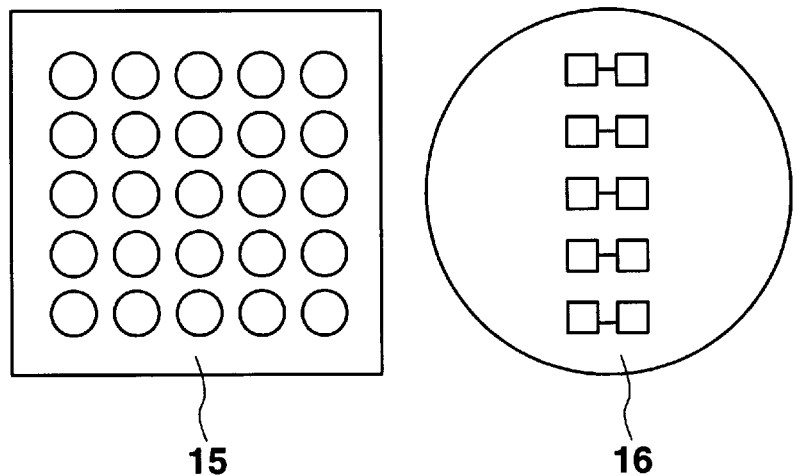
FIG. 2 schematically shows a spatial arrangement of a plurality of samples disposed in the form of a matrix as well as an associated sensor line.

In particular it is also possible for a plurality of samples, e.g. as shown in FIG. 2, to be disposed in the form of a sample matrix 15 and simultaneously investigated using a multichannel measurement system. Towards this end the sensors can be disposed in a single plane e.g. in the form of an array or of a sensor line 16. This measurement configuration is likewise suitable for detection of the spatial distribution of analytes as is e.g. particularly advantageous in in vivo measurements.

A rapid change of the magnetic field in the sample volume must be guaranteed in order to detect analytes through measurements of the relaxation of the analyte magnetization. The more rapid the fields change, the smaller the relaxation time which can be detected.

A measurement cycle can proceed as follows:

1) Production of a magnetizing field with the excitation coil 11. The sample 12 should be located in the magnetic field below one of the field coils of the sensor gradiometer 10.

2) Switching-off of the magnetic field and measurement of the signal present at the output of the FLL-regulation electronics 1. It is advantageous when the SQUID can be operated during the entire process in FLL-mode. In the event that the speed of change of the magnetic field gradient at the sensor gradiometer 10 is larger than the speed of change of the output signal of the FLL-electronics, the regulation loop should be first closed shortly after switch-off of the magnetizing field. This can also occur automatically when reaching the regulating region.

3) The time dependence of the SQUID output signal can then be analyzed e.g. by a computer.

4) After decay of the transient processes, the procedures 1) and 2) can be repeated in order to be able to obtain an average value. This can be carried out repeatedly using magnetizing fields of opposite polarity.

5) If appropriate an additional measurement cycle can be repeated below the other sensor gradiometer 10 field coil.

6) The next sample can, possibly automatically, be positioned and measured below the sensor gradiometer field recording coil.

7) It is also possible to carry out simultaneous comparison measurements between two samples, by positioning one sample below each planar gradiometer field coil.

It may be appropriate to carry out a calibration cycle before a measurement. Towards this end the measurement cycle is carried out without a measuring sample or with a corresponding calibrating sample. The reference measurements thereby obtained can be utilized to correct the sample measurement.

Measurement of the binding remanence can likewise be carried out with the above described apparatus to detect analytes through measurement of the remanence magnetization. A possible measurement procedure is described below:

a) The sample disposed in or below one of the field recording coils of the sensor gradiometer is magnetized periodically (at low frequency) with opposing direction and possibly changing amplitude of the magnetic field. A ramp-shaped time dependence of the magnetization is advantageous (Advantages: maximum signal change speed of the FLL-electronics is not exceeded and the sensor gradiometer can be operated during the entire measurement cycle in FLL-mode). Pauses remain between the magnetizing phases during which the sample is not exposed to an excitation field.

b) The FLL-electronics remains in regulation mode during the entire measurement cycle. Interfering transients are detected by means of the possibly substantially faster reference gradiometer and are directly coupled back into the sensor gradiometer.

c) A slight detuning of the sensor gradiometer can simultaneously provide a measurement of the field amplitude.

d) Remanent residual field produced by the sample can be measured in the magnetizing pauses.

The described reversal of the exciting field can facilitate compensation of the interference field drift processes. The sample can be moved during the measurement in order to improve the signal-to-noise ratio (vibration, rotation, ultrasound, hydraulic, trap door and the like). This can be facilitated by non-magnetic extensions of elevating platforms, linear motors and the like. In constructing the apparatus, one should avoid all ferromagnetic impurities which could falsify measured results.

Figure 3:
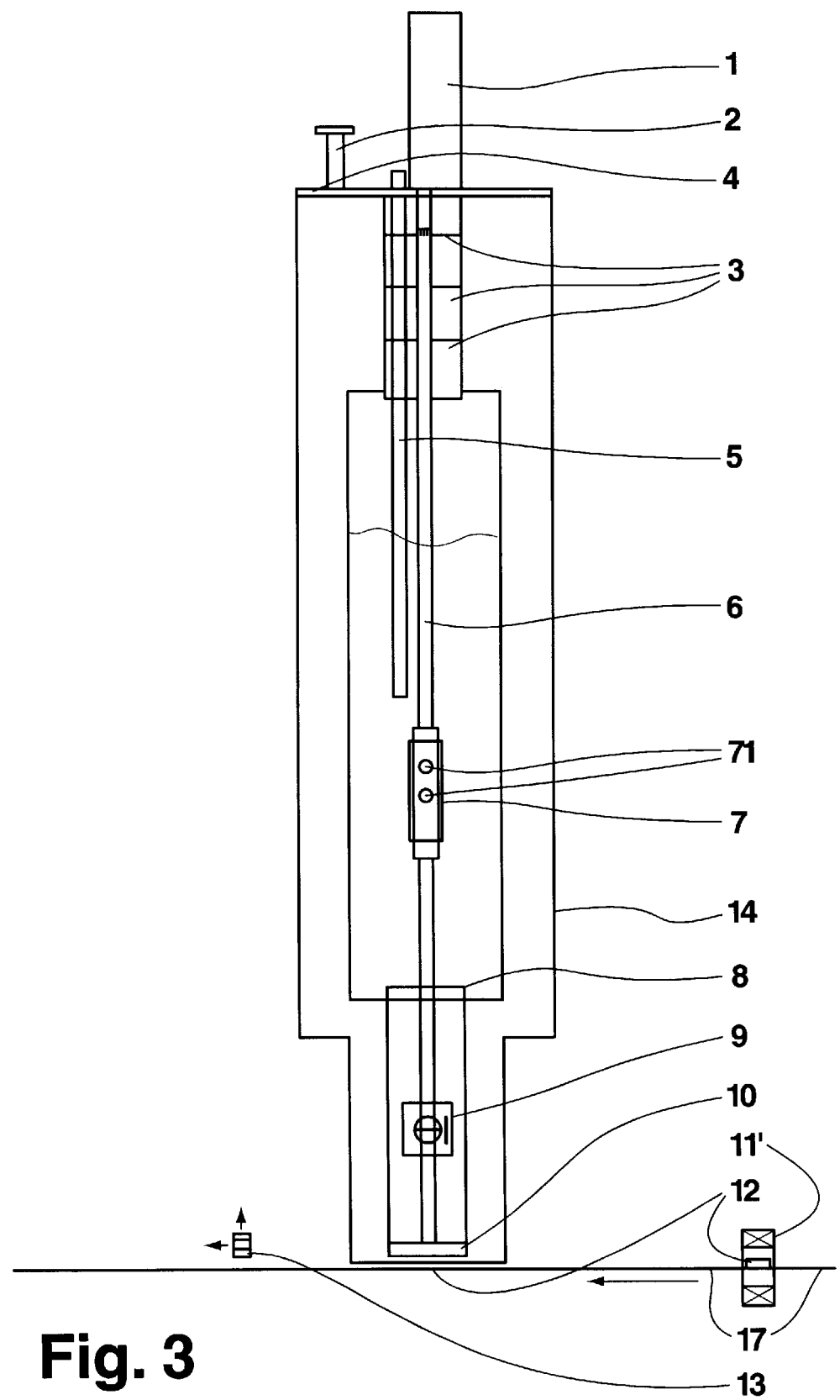
FIG. 3 shows a schematic cut representation of a second embodiment of the apparatus in accordance with the invention.

Instead of magnetizing the sample in the measurement volume, the magnetizing can occur spatially separated from the detection device as represented in FIG. 3.:

In this case the sample 12 is transported from the site of the magnetizing device, where same is magnetized in the excitation coil 11', to the measuring location by means of a mechanism e.g. using a conveyor belt 17. This mechanism can simultaneously be used to change the samples 12. In addition, the above mechanism produces a modulation of the magnetic field generated by the sample at the location of the field recording coil.

In addition, the following additional means for suppression of interfering fields can be utilized:

A triaxial vector magnetometer 9 or a vector gradiometer can be utilized to produce reference signals which consists essentially of three mutually orthogonal SQUID magnetometers disposed at the sides of a cube with each being operated in FLL-mode. Suppression of interferences is achieved through appropriate weighted subtraction of the reference signals from the gradiometer output signal. This can advantageously transpire in two steps. Manual compensation of weighted output signals of the vector magnetometer 9 and the sensor gradiometer 10 reduces the dynamic range of the measured signal for subsequent A/D conversion and processing by a computer. In a second stage, the individual signals of the vector magnetometer 9 are combined with the assistance of appropriate algorithms in such a fashion that a maximum interference suppression is achieved in the measured signal. This can be accomplished by matched optimized filters which take into consideration the existing correlation between the signals.

Appropriate offset compensation is provided for each signal prior to A/D conversion in order to optimize the dynamic range of the converter. Should the vector magnetometer 9 have small SQUID inductance, regulation band widths in the FLL-mode of several MHz can be achieved to also regulate-out and compensate for transient interference.

Figure 4:
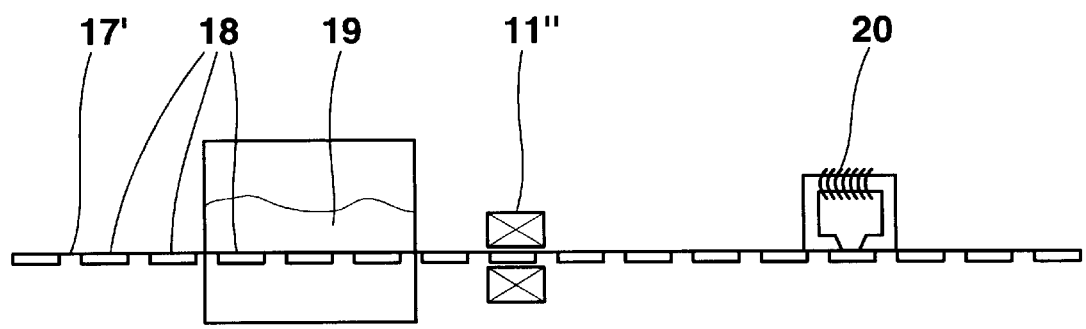
FIG. 4 shows a schematic cut representation of a third embodiment of the apparatus in accordance with the invention.

As an alternative to the above described apparatus, bound remanent particles can also be measured on an appropriately prepared conveyor belt 17' by passing the belt by a magnetic field sensor 20 (analogous to magnetic tape technology) as shown in FIG. 4. A belt 17' prepared e.g. with antigens 18 is moved through a bath 19 containing antibodies marked with remanent particles, subsequently magnetized through a suitable exciting coil 11", and then passed by a magnetic field sensor 20. It is particularly advantageous to produce a structure by means of appropriate periodically disposed coating of the belt 17' e.g. with antigens 18 which leads to alternating regions of bound remanent particles and free regions to produce a defined periodicity.

The above effect can also be achieved with a continuous coating of the belt 17' if the belt prepared with bound remanent particles is moved through an alternating magnetic field (again analogous to magnetic tape technology). Both procedures mentioned above lead to a signal on the magnetic field sensor 20 of known frequency and binding-dependent amplitude and can advantageously be measured by means of e.g. lock-in-measuring technology. The technology utilized is similar to that of a tape recorder.

An apparatus can be utilized which deviates slightly from the apparatus described in FIG. 1 in order to measure complex frequency-dependent magnetic material properties:

A magnetizing device is advantageous which produces a homogeneous magnetizing field at the location of the field recording coils of the sensor gradiometer. The homogeneous magnetic field is advantageously directed along the direction of lowest field sensitivity of the field recording coils and can be produced e.g. with a Helmholtz coil configuration 21. Analogous to the above described compensation methods, the sensor gradiometer can be adjusted for minimum sensitivity to the excitation field.

The magnetizing device is fed with an alternating current of variable frequency (taking into consideration the skin effect and the frequency-dependent dispersion of the excitation coil). The time-dependent magnetization measured by the magnetic field sensors is advantageously analyzed by means of lock-in-technology in rigid phase relationship to the likewise measured exciting field strength H. In this fashion, the magnitude and the phase of the magnetization M of the sample can be determined for the corresponding excitation frequency. A comparison to reference measurements of unbound analytes leads to high sensitivity measurement of analyte binding.

Figure 5:
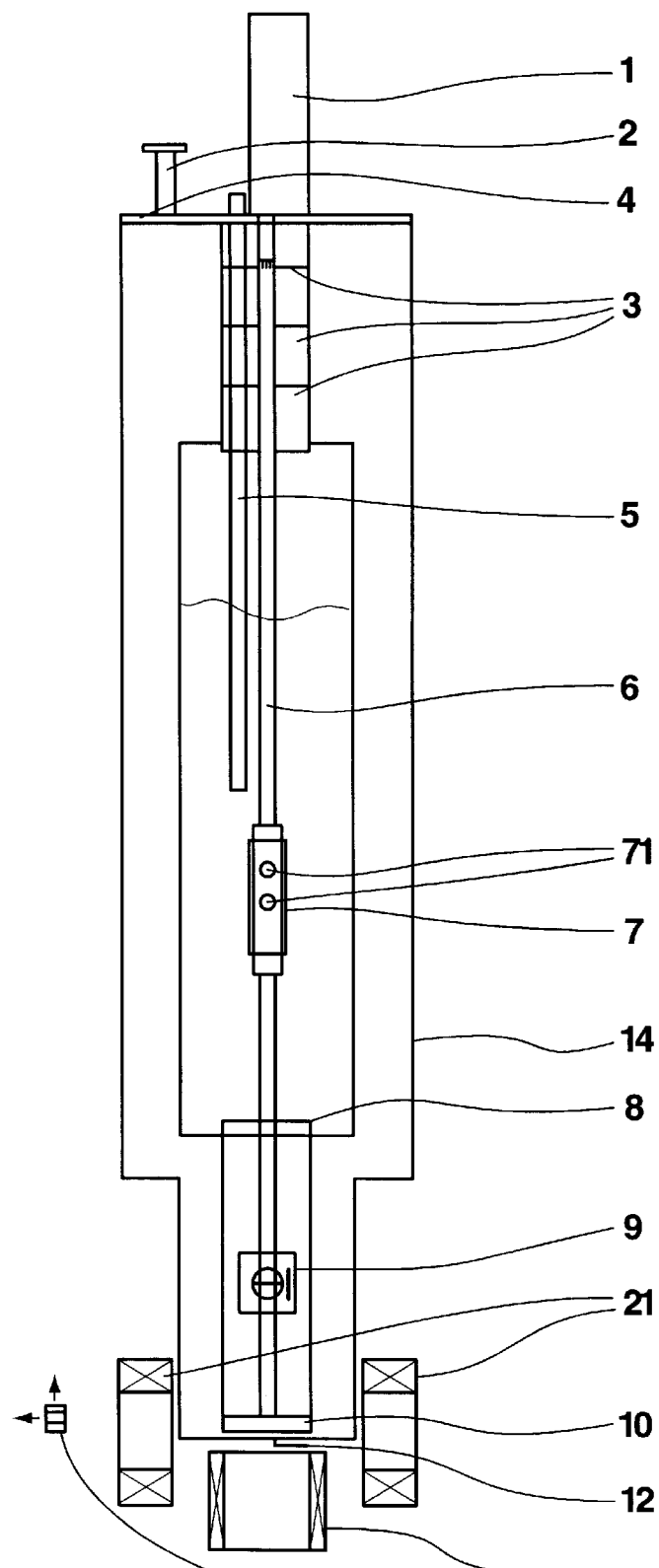
FIG. 5 shows a schematic cut representation of a fourth embodiment of the apparatus in accordance with the invention.

Finally, the combination apparatus represented in FIG. 5 can be used to measure analyte binding using each of the methods I, II, and III. A Helmholtz coil 21 is additionally provided for susceptibility measurements. An apparatus of this type serves for the quantitative detection of analytes in fluid and solid phase by means of relaxation measurements, binding remanence measurements as well as by means of frequency-dependent complex magnetic material properties.

The above described embodiments of the apparatus in accordance with the invention, in particular those with which the detection device comprises a device for measurement of the binding remanence and/or the magnetorelaxometric detection, can also be specially configured for in vivo measurements on people or animals.

What is claimed is:

1. An apparatus for the measurement of analytes in a sample by means of receptor ligand bonding, the apparatus comprising:

a detection device for measurement of magnetic properties of a sample during a measurement time;

a magnetizing device for producing a magnetic field at the sample; and means for reducing a magnetic field strength of said magnetic field at the sample by a factor of at least 10 during said measurement time.

2. The apparatus of claim 1, wherein said factor is at least 1000.

3. The apparatus of claim 1, wherein said reducing means comprise means for moving the sample during said measurement time.

4. The apparatus of claim 1, wherein said reducing means comprise a circuit for switching-off said magnetic field at the sample for a predetermined time, and a device for moving the sample during said measurement time.

5. The apparatus of claim 1, wherein said reducing means comprises a switching device for switching-off said magnetic field for a predetermined length of time, said switching device having a first member to switch-on and switch-off said magnetic field and having a second member for switching-on and switching-off said detection device.

6. The apparatus of claim 5, wherein said first and said second members can be switched independently of each other.

7. The apparatus of claim 5, wherein said first member can be switched with a predetermined fixed time correlation with respect to said second member.

8. The apparatus of claim 5, wherein said first member can reduce predetermined field amplitudes and field polarities of said magnetic field produced by said magnetizing device.

9. The apparatus of claim 8, wherein said first member for producing predetermined amplitude time dependences and predetermined polarity time dependences of said magnetic field produced by said magnetizing device.

10. The apparatus of claim 1, wherein said detection device comprises means for measurement of a magnetization of the sample.

11. The apparatus of claim 10, wherein said detection device comprises means for magneto-relaxometric detection.

12. The apparatus of claim 1, wherein said detection device comprises means for measurement of a binding remanence of the analyte in the sample.

13. The apparatus of claim 1, wherein said detection device comprises at least one superconducting quantum interference device.

14. The apparatus of claim 1, wherein said detection device comprises at least one induction coil.

15. The apparatus of claim 1, further comprising means for electronic suppression of interfering signals.

16. The apparatus of claim 15, wherein said means for electronic suppression of interfering signals comprises a unit for adaptive filtering.

17. The apparatus of claim 1, further comprising means for vector measurement of interfering fields and means connected thereto for appropriate compensation of at least one of a signal measured by said detection device and said magnetic field produced by said magnetizing device.

18. The apparatus of claim 1, wherein the sample for in-vivo measurements.

* * * * *